US012678314B2

(12) United States Patent
Loh et al.

(10) Patent No.: US 12,678,314 B2
(45) Date of Patent: Jul. 14, 2026

(54) ADAPTIVE AND VARIABLE STIFFNESS ANKLE BRACE

(71) Applicants: THE REGENTS OF THE UNIVERSITY OF CALIFORNIA, Oakland, CA (US); THE UNITED STATES OF AMERICA, AS REPRESENTED BY THE SECRETARY OF THE NAVY, Silver Spring, MD (US); THE GOVERNMENT OF THE UNITED STATES, AS REPRESENTED BY THE SECRETARY OF THE ARMY, Fort Detrick, MD (US)

(72) Inventors: Kenneth Loh, San Diego, CA (US); Yingjun Zhao, La Jolla, CA (US); Yujin Park, Austin, TX (US); John Fraser, San Diego, CA (US); Shawn Farrokhi, Fort Detrick, MD (US); Pinata Sessoms, San Diego, CA (US); Amy Silder, San Diego, CA (US); Adam Yoder, Fort Detrick, MD (US)

(73) Assignees: THE REGENTS OF THE UNIVERSITY OF CALIFORNIA, Oakland, CA (US); THE GOVERNMENT OF THE UNITED STATES, AS REPRESENTED BY THE SECRETARY OF THE ARMY, Oakland, CA (US); THE UNITED STATES OF AMERICA, AS REPRESENTED BY THE SECRETARY OF THE NAVY, Silver Springs, MD (US)

( * ) Notice: Subject to any disclaimer, the term of this patent is extended or adjusted under 35 U.S.C. 154(b) by 14 days.

(21) Appl. No.: 18/700,231

(22) PCT Filed: Oct. 11, 2022

(86) PCT No.: PCT/US2022/046321
§ 371 (c)(1),
(2) Date: Apr. 10, 2024

(87) PCT Pub. No.: WO2023/064303
PCT Pub. Date: Apr. 20, 2023

(65) Prior Publication Data
US 2025/0221839 A1 Jul. 10, 2025

Related U.S. Application Data

(60) Provisional application No. 63/254,474, filed on Oct. 11, 2021.

(51) Int. Cl.
*A61F 5/01* (2006.01)
*A61L 15/12* (2006.01)

(52) U.S. Cl.
CPC .......... *A61F 5/0111* (2013.01); *A61F 5/0109* (2013.01); *A61F 5/0118* (2013.01); *A61L 15/12* (2013.01)

(58) Field of Classification Search
CPC ........ A61F 5/01; A61F 5/0102; A61F 5/0104; A61F 5/0106; A61F 5/0109; A61F 5/0111; A61F 5/0118; A61L 15/12
See application file for complete search history.

(56) References Cited

U.S. PATENT DOCUMENTS

2012/0181896 A1 7/2012 Kornbluh et al.
2015/0018733 A1 1/2015 Ben-Meir et al.
(Continued)

OTHER PUBLICATIONS

International Search Report and Written Opinion mailed Jan. 31, 2023 for PCT/US2022/046321.

*Primary Examiner* — Keri J Nelson
(74) *Attorney, Agent, or Firm* — Sheppard, Mullin, Richter & Hampton LLP

1800

(57) ABSTRACT

Embodiments of the presently disclosed technology provide orthopedic braces that employ adaptive/variable stiffness metamaterials to emulate the strain-stiffening behavior of ligaments. These orthopedic braces may provide lower rigidity during low-demand/low-strain activities (e.g., normal gait movements) and increased rigidity under high-demand/high-strain activities (e.g., running and other movements that require larger ranges of motion and rotational velocities).

20 Claims, 19 Drawing Sheets

(56) References Cited

U.S. PATENT DOCUMENTS

2021/0154038 A1* 5/2021 Koch ...................... B29C 64/00
2021/0236319 A1 8/2021 Teng et al.

* cited by examiner

DIMENSION OF THE HONEYCOMB-SHAPED STRUCTRES

| GEOMETRY | RING SIZE (r) [mm] | WALL THICKNESS (w) [mm] | THICKNESS [mm} |
|---|---|---|---|
| H | 10 | 1 | 2 |
| $r_1$ | 11 | 1 | 2 |
| $r_2$ | 12 | 1 | 2 |
| $w_1$ | 10 | 2 | 2 |
| $w_2$ | 10 | 3 | 2 |
| $t_1$ | 10 | 1 | 1 |
| $t_2$ | 10 | 1 | 3 |
| $t_3$ | 10 | 1 | 4 |

MOONEY-RIVLIN PARAMETER OF 3D-PRINTED TPU

302

| $C_{10}$ [MPa] | $C_{01}$ [MPa] | $C_{11}$ [MPa] | $C_{20}$ [MPa] | $C_{02}$ [MPa] | $P$ [kg/m³] |
|---|---|---|---|---|---|
| -12.8 | 19.8 | -0.93 | 0.0557 | 4.25 | 1200 |

ANTERIOR
TALOFIBULAR
LIGAMENT
*ATFL*

CALCANEO
FIBULAR LIGAMENT
*CF*

TIBIA

FIBULA

TALUS

POSTERIOR
TALOFIBULAR
LIGAMENT
*PTFL*

ALCANEUS

TOP VIEW

SIDE VIEW

*1602*

*1604*

ADAPTIVE AND VARIABLE STIFFNESS ANKLE BRACE

REFERENCE TO RELATED APPLICATIONS

The present application is a U.S. national phase of PCT International Patent Application No. PCT/US2022/046321, filed Oct. 11, 2022 and titled "ADAPTIVE AND VARIABLE STIFFNESS ANKLE BRACE", which claims priority to U.S. Provisional Patent Application No. 63/254,474, filed Oct. 11, 2021 and titled "Adaptive and Variable Stiffness Ankle Brace," which are incorporated herein by reference in their entireties.

TECHNICAL FIELD

Various embodiments generally relate to medical devices. More particularly, various embodiments are related to adaptive and variable stiffness ankle braces.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

Lateral ankle sprains cost billions of dollars in medical expenses annually and frequently result in long-term functional decline and a diminished health-related quality of life. While ankle braces have been shown to be effective in prophylaxis of subsequent ankle sprains, current braces are often either (a) too stiff, and affect normal gait or (b) too flexible, and provide insufficient support during high-intensity activities. Accordingly, the rigidity and poor fit of conventional ankle braces may often lead to discomfort and low compliance. Rigidity of orthopedic braces worn over other ligament regions (e.g., knee braces, elbow braces, wrist braces, etc.) often causes the same/similar discomfort—also resulting in reduced wear compliance.

Against this backdrop, embodiments of the presently disclosed technology provide orthopedic braces that employ adaptive/variable stiffness metamaterials to emulate the adaptive strain-stiffening behavior of ligaments (as used herein "strain-stiffening" may refer to a mechanical property where stiffness of a structure/material increases upon increased deformation/strain). Like many ligaments, these orthopedic braces may exhibit lower stiffness/rigidity during low-demand/low-strain activities (e.g., walking and other normal gait movements) and increased stiffness/rigidity during high-demand/high-strain activities (e.g., running and other movements that require larger ranges of motion and rotational velocities). Accordingly, orthopedic braces in accordance with embodiments of the presently disclosed technology may provide greater comfort during normal, low-demand activities than existing orthopedic braces which maintain a high level of stiffness/rigidity during all activities. Relatedly, embodiments may provide greater support during high-demand activities than existing orthopedic braces which maintain a low level of stiffness/rigidity during all activities. By providing greater comfort during normal, low-demand activities, and greater support during high-demand activities, embodiments can improve wear compliance and reduce the incidence of repetitive injuries.

Figure 17:
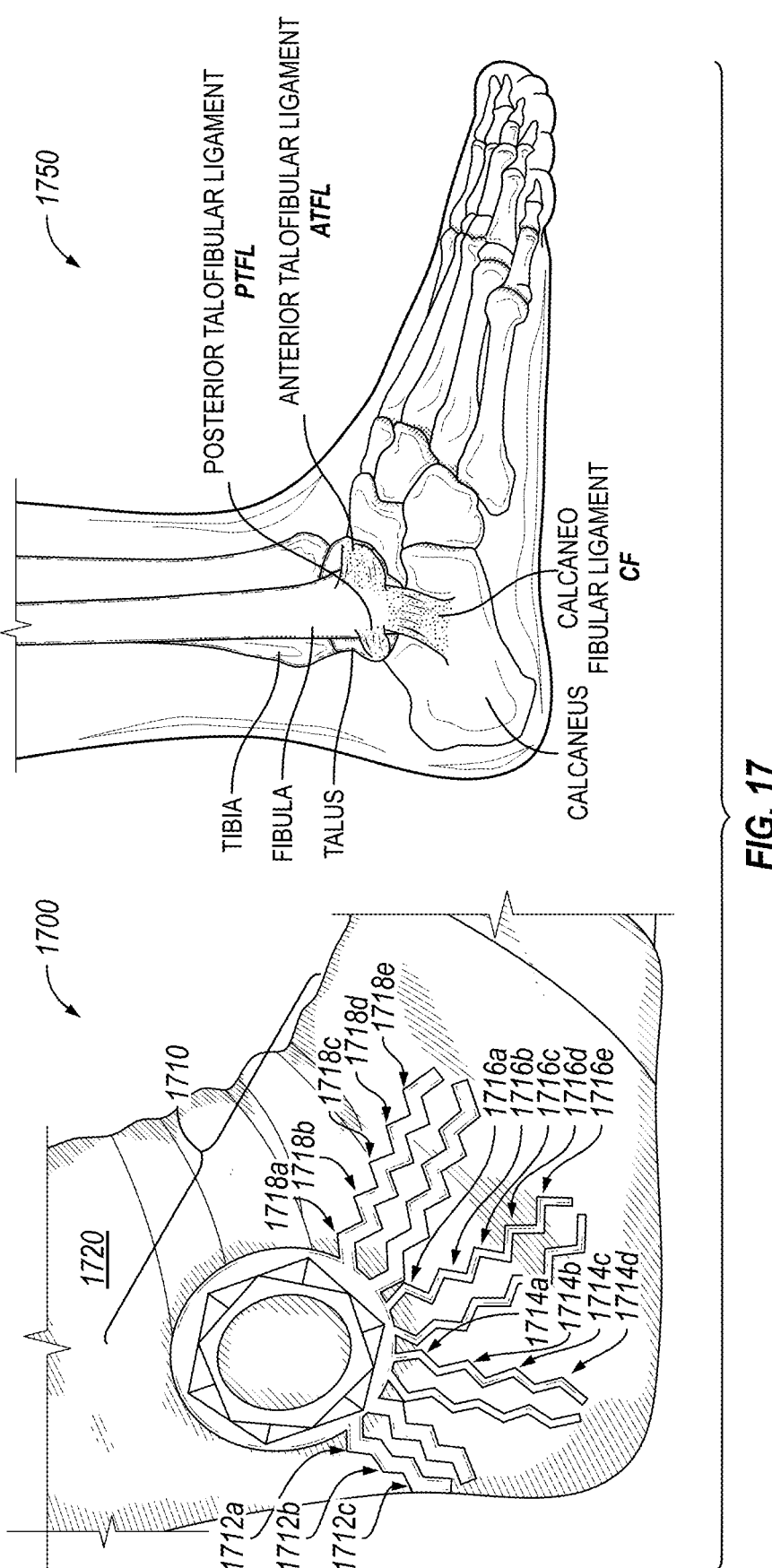
FIG. 17 illustrates an example adaptive-stiffness ankle brace compared to an example diagram of an ankle ligament region, in accordance with embodiments of the disclosed technology.

Certain embodiments provide an adaptive-stiffness brace comprising: (1) a flexible sleeve to be worn over a ligament region (e.g., an ankle, a knee, and elbow, a wrist, etc.); and (2) an adaptive-stiffness metamaterial coupled to the flexible sleeve. The adaptive-stiffness metamaterial may comprise a plurality of adjacent unit cells arranged on the flexible sleeve to emulate strain-stiffening behavior of ligaments in the ligament region (as used herein a "metamaterial" or "mechanical metamaterial" may refer to a structure comprised of adjacent unit cells arranged to yield/exhibit a desired mechanical characteristic-mechanical characteristics of mechanical metamaterials tend to depend highly on unit cell geometry). In certain examples, embodiments can emulate the strain-stiffening behavior of ligaments in a ligament region by arranging the plurality of adjacent unit cells in a manner that emulates the location/orientation of ligaments in the ligament region (here it may be noted that experiments conducted in accordance with embodiments of the presently disclosed technology demonstrated that such arrangement for the unit cells yielded strain-stiffening behavior that closely resembles strain-stiffening behavior of ligaments in a ligament region). For example, as depicted in FIG. 17, an example adaptive-stiffness ankle brace 1700 may include a plurality of adjacent unit cells arranged in a manner that emulates the location and orientation of ankle ligaments. In particular: the arrangement of adjacent unit cells 1712(*a*)-(*c*) emulates the location/orientation of the posterior talofibular ligament (PTFL); the arrangement of adjacent unit cells 1714(*a*)-(*d*) and 1716(*a*)-(*e*) emulate the location/orientation of the larger calcaneofibular ligament (CF); and the arrangement of adjacent unit cells 1718(*a*)-(*e*) emulate the location/orientation of the anterior talofibular ligament (ATFL). As alluded to above, by closely emulating the strain-stiffening behavior of ligaments, embodiments can provide a more comfortable/natural fit than existing orthopedic braces.

In some embodiments, the plurality of adjacent unit cells of the adaptive-stiffness metamaterial may comprise a plurality of adjacent hexagonal ring-shaped unit cells (it should be understood that the plurality of adjacent unit cells may comprise a variety of different shapes/patterns such as hexagonal rings, hexagonal rings with rounded edges, rectangular rings, rectangular rings with turning points, circular rings, hour glass-shaped rings, etc.). As described below, example experiments conducted in accordance with the presently disclosed technology demonstrate that such a hexagonal ring-shaped unit cell structure yields strain-stiffening behavior that closely resembles/emulates strain-stiffening behavior of ligaments such as ankle ligaments. In these examples, one or more of the hexagonal ring-shaped unit cells may be "multi-walled" where e.g., a first hexagonal ring is concentrically located within a second hexagonal ring. In certain cases, these multi-walled unit cells may more closely emulate strain-stiffening behavior of ligaments (e.g., ankle ligaments) than single-walled unit cells.

The adaptive-stiffness metamaterial may comprise various types of materials. In certain embodiments, the adaptive-stiffness metamaterial may comprise a flexible polymer material such as thermoplastic polyurethane. In some embodiments, the adaptive-stiffness metamaterial may be coupled to the flexible sleeve at junctions of adjacent unit cells. Anchoring/coupling the adaptive-stiffness metamaterial to the sleeve at junctions of adjacent unit cells enables embodiments to control the direction and orientation of strain stiffening behavior. This can also enable alignment of the adaptive-stiffness component to the appropriate ligament (s).

As alluded to above, in various embodiments, an adaptive/variable stiffness structural component (i.e., metamaterial) may be integrated to form an adaptive stiffness ankle brace which mimics the nonlinear and viscoelastic behavior of ankle ligaments. The brace's mechanical properties may be engineered via proper material selection and geometrical optimization. For example, topology optimization (TO) may be performed to design and incorporate the adaptive material into a flexible brace skeleton, thereby eliminating unnecessary material and simultaneously ensuring the brace can be comfortably fitted inside a standard military boot. Unique geometrical patterns (e.g., hexagonal rings, hexagonal rings with rounded edges, rectangular rings, rectangular rings with turning points, circular rings, hour glass-shaped rings, etc.) can be three dimensionally (3D) printed to form the variable stiffness polymeric structural component. To further fine tune their stiffness profile, different metamaterial geometries may designed and tested, and their load-displacement curves may be compared. Accordingly, an optimized component may be assembled onto a sleeve brace to provide adaptive mechanical support under different ankle movements. In some embodiments, laboratory testing of the brace may be conducted using an isokinetic dynamometer fitted with a phantom ankle-foot complex, whereby the forces and rotational velocities representative of an injury can be imposed while measuring brace response.

In certain embodiments, mechanical metamaterials may be employed to design an adaptive stiffness material to specifically exhibit strain-stiffening behavior. Mechanical metamaterials may consist of adjacently arranged unit cells that can be designed to yield a desired behavior exploiting motion, deformations, stresses, and mechanical energy. Unlike solid geometries (e.g., pipes, bars, and dog bones), mechanical properties of mechanical metamaterials tend to depend highly on unit cell geometry. Accordingly, various embodiments may employ a mechanical metamaterial/unit cell structure design that exhibits adaptive stiffness properties.

For example, in certain embodiments, a honeycomb (i.e., hexagonal) geometry may be designed and three dimensionally printed with thermoplastic polyurethane (TPU). This honeycomb geometry may exhibit non-linear, strain-stiffening (in certain cases the strain-stiffening behavior may be non-linear), elastic behavior. Such behavior may closely resemble the published stress-strain response of the three most commonly injured ligaments of the ankle-foot. Said differently, various embodiments which incorporate this honeycomb geometry may exhibit minimal-load shape change similar to how ligaments behave under low range of motion ("ROM"). For example, the shape of the honeycomb structure may change under lower loads until certain elements fully straighten. Then, the straightened elements may be engaged to bear loads with the material being strained, which can result in rapid stiffness increase. In certain embodiments, the mechanical responses of various honeycomb geometries may be compared with that of a conventional rectangular geometry.

In certain embodiments, different material designs may be mathematically modelled to optimize mechanical strength and force-strain profiles to match estimated ligamentous loads from an injurious event. For example, a composite material in accordance with various embodiments may developed which is optimized to dynamically increase stiffness in response to applied force. As alluded to above, the material may be 3D-printed with TPU in a 2D honeycomb-shaped geometry. To optimize its mechanical properties for use in an ankle brace, variations in the 2D honeycomb-shaped geometry (i.e., ring size, length of lateral elements, and thickness) may be simulated using finite element models. Material coupons may be printed and tested using controlled laboratory load testing. Accordingly, a low-profile, flexible, and lightweight material that will deliver variable force and rigidity in response to different applied forces and strain rates may be developed. As alluded to above, this type of material design may remain flexible during low-demand activities (e.g., walking) but provide greater levels of support and rigidity during activities involving greater ankle ranges of motion and rotational velocities (e.g., running).

As will be described in greater detail below, example experiments were performed to test various embodiments. For example, a series of tensile load tests were performed on different honeycomb unit cell configurations. In these example experiments, the influence of unit cell designs on mechanical strength and force-strain profiles was characterized. Experimentally calibrated finite element models of individual components simulated the mechanical response of the geometry, which were then used to optimize the geometrical parameters of the honeycomb shape (i.e., ring size, length of lateral elements, and thickness). The experimental results identified promising design parameters for honeycomb geometries that may be used to realize next-generation adaptive ankle braces, in accordance with various embodiments of the presently disclosed technology.

Example Experiments Section

As alluded to above, conventional ankle braces typically leverage rigid materials, which usually are linearly elastic and have high stiffness to provide sufficient mechanical support during high ankle ROM. However, they restrict ankle movement during low ROM and can impact the wearer's comfort. On the contrary, during low ROM activities, human ankle ligaments act to stabilize the joints and have lower movement restriction. Therefore, various embodiments improve conventional brace designs by constructing load-bearing elements with ligament-like materials that exhibit adaptive stiffness.

Accordingly, in example experiments, mechanical metamaterials were employed to design an adaptive stiffness material to specifically exhibit strain-stiffening behavior. These exampled experiments, along with their results, are detailed below.

Sample Fabrication

Figure 1:
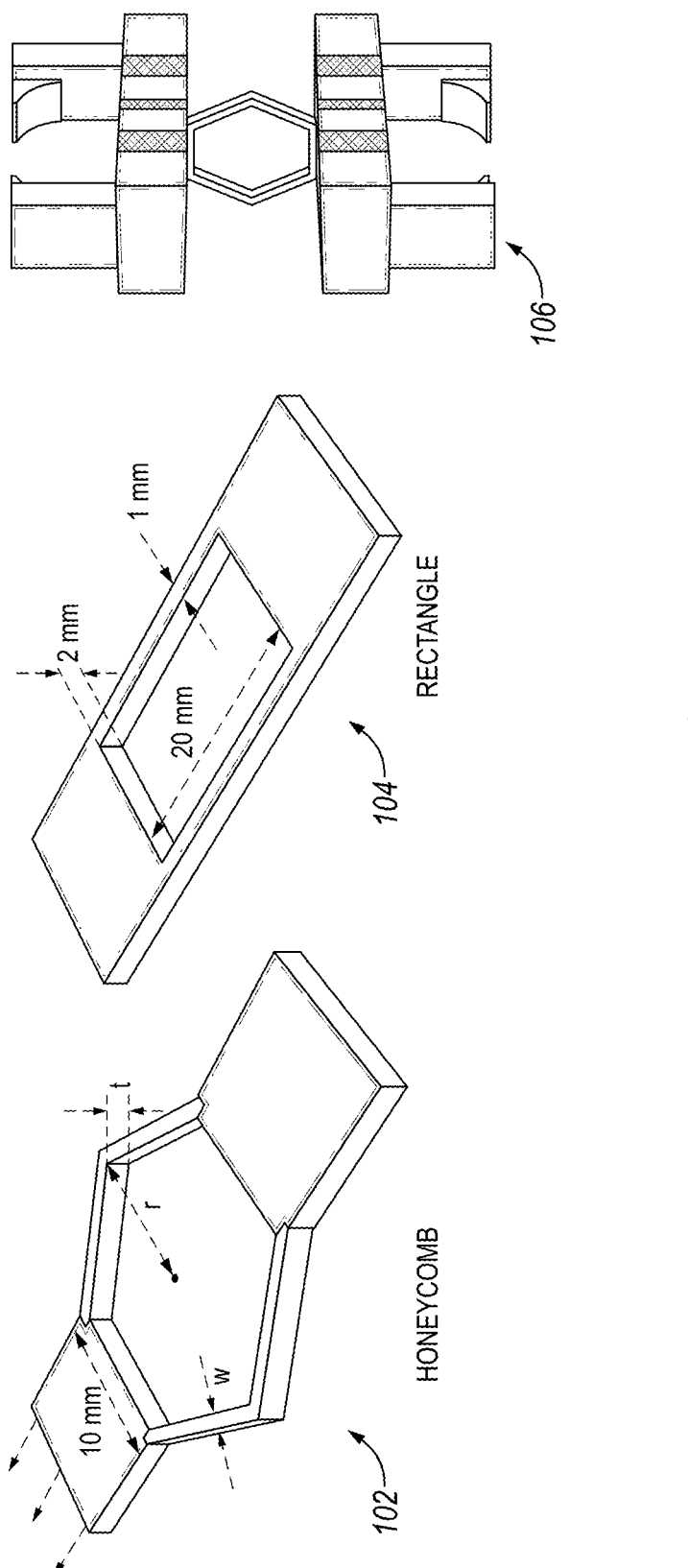
FIG. 1 depicts example metamaterial geometries that were fabricated in example experiments conducted in accordance with embodiments of the disclosed technology.

FIG. 1 illustrates example unit cell geometries that were fabricated in the example experiments. Diagram 102 illustrates an example honeycomb geometry, diagram 104 illustrates an example rectangle geometry, and diagram 106 illustrates a uniaxial tensile test setup that was used in the example experiments.

In the example experiments, Thermoplastic polyurethane (TPU 95A) and a commercial fused deposition modeling 3D printer, Ultimaker 3+ (Ultimaker, Utrecht, The Netherlands), were used to print the unit cell geometries illustrated by FIG. 1. TPU was selected not only for its flexible, linear elastic nature but also because of its intrinsic energy absorbing properties. A 3D model file (*.stl) of each geometrical design was created in Fusion 360 (Autodesk, Inc., San Rafael, CA, USA) and then imported to Ultimaker Cura 4.5 for 3D printing. In the example experiments, 3D printing was restricted to the lines infill pattern at 45° and −45° angles and 100% density. Gripping tabs were printed at both ends of the specimens for tensile tests.

In the example experiments, the stiffness of the honeycomb geometry was adjusted by varying geometrical parameters, such as the honeycomb ring size (r), wall thickness (w), and substrate thickness (t), as illustrated by diagram

102. The width of the coupon grips and the honeycomb ring depth were affixed at 10.0 and 17.3 mm, respectively. Eight different honeycomb geometries were 3D printed.

Figure 2:
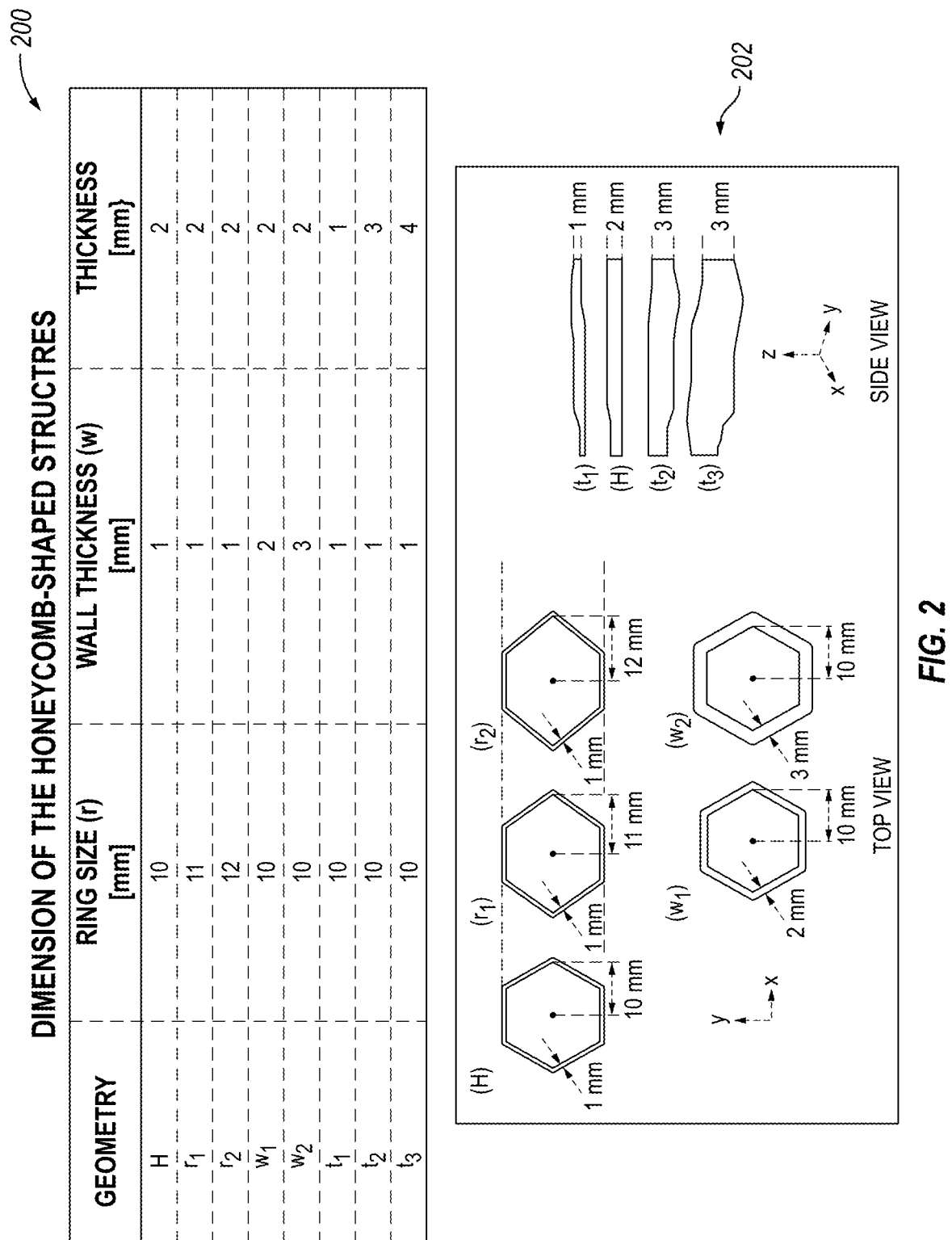
FIG. 2 depicts the names and geometrical dimensions of honeycomb geometries which were fabricated in example experiments conducted in accordance with embodiments of the disclosed technology.

FIG. 2 contains a table (table 200) and a diagram (diagram 202) which depict the names and geometrical dimensions of the honeycomb geometries which were fabricated in the example experiments described in conjunction with FIG. 1.

Tensile Testing Methods

As alluded to above, diagram 106 of FIG. 1 illustrates the uniaxial tensile test setup used in the example experiments. Here the printed unit cell geometries were tested using a TestResources 150R load frame (TestResources, Inc., Shakopee, MN, USA) equipped with a 100 N load cell. Each specimen was loaded in its longitudinal direction at a constant strain rate of 0.1 mm/s until the total displacement reached 30.0 mm. The load and displacement profiles were recorded simultaneously. The recorded profiles were analyzed up to 20% strain.

Numerical Modeling

Figure 3:
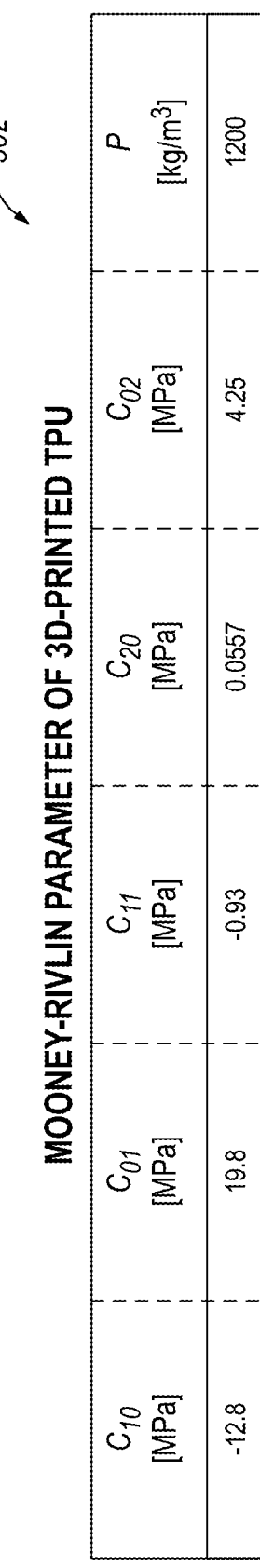
FIG. 3 depicts a table which illustrates data from example experiments conducted in accordance with embodiments of the disclosed technology.

In the example experiments, the stress distribution of the honeycomb geometry was calculated using experimentally calibrated finite element (FE) simulations. To obtain representative material properties of the actual specimens fabricated, dog bone-shaped TPU coupons were 3D printed and subjected to uniaxial tensile tests. A nonlinear least-squares regression fit was applied to obtain the five Mooney-Rivlin parameters listed in table 302 of FIG. 3 for modeling incompressible, hyperelastic materials. The first Piola-Kirchhoff stress expression for uniaxial deformation is as follows:

$$P = 2\left(1 - \lambda^{-3}\right)\left(\lambda C_{10} + 2C_{20}\lambda\left(I_{1_{uni}} - 3\right) + \right. \tag{1}$$

$$\left. C_{11}\lambda\left(I_{2_{uni}} - 3\right) + C_{01} + 2C_{02}\left(I_{2_{uni}} - 3\right) + C_{11}\left(I_{1_{uni}} - 3\right)\right)$$

These parameters were applied to a COMSOL Multiphysics® (COMSOL Inc., Stockholm, Sweden) hyperelastic FE model to calculate the stress distribution of honeycomb geometries subjected to uniaxial tensile loads.

Geometrical Design and Load-Free Shape Change

In the example experiments, honeycomb geometries with different r's were subjected to uniaxial tensile loads to test their ability to mimic the nonlinear behavior of human ankle ligaments under low ROM. The load-strain profile of the honeycomb and rectangular (Rec) geometries are shown in graph 400 of FIG. 4. In these example experiments, the rectangular geometry was immediately engaged to bear loads as soon as load was applied, while the honeycomb geometries were not engaged until the honeycomb ring shape was fully extended. In the experiments, the geometry with a higher r was able to sustain minimal-load shape change over larger applied deformations. This may be because the total length of all the ring segments was longer (see geometries H, $r_1$, and $r_2$ in table 200 of FIG. 2).

Figure 5:
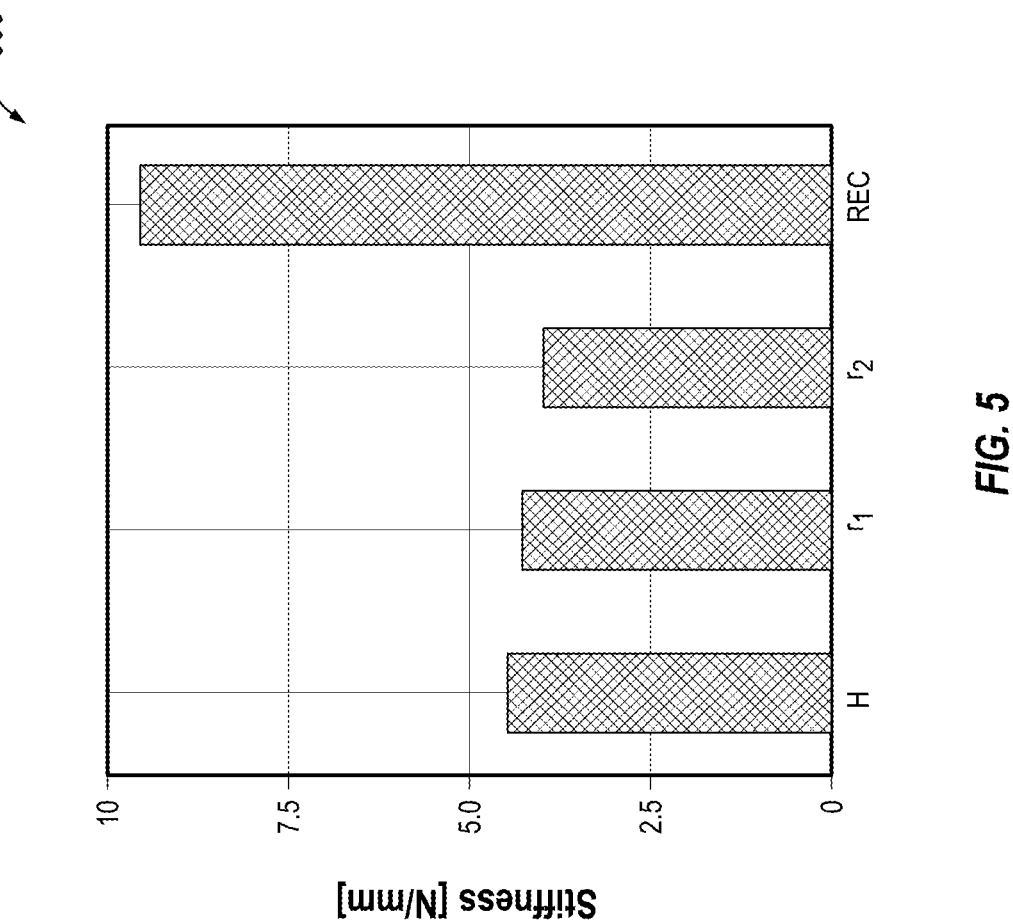
FIG. 5 depicts a graph which illustrates data from example experiments conducted in accordance with embodiments of the disclosed technology.
Figure 6:
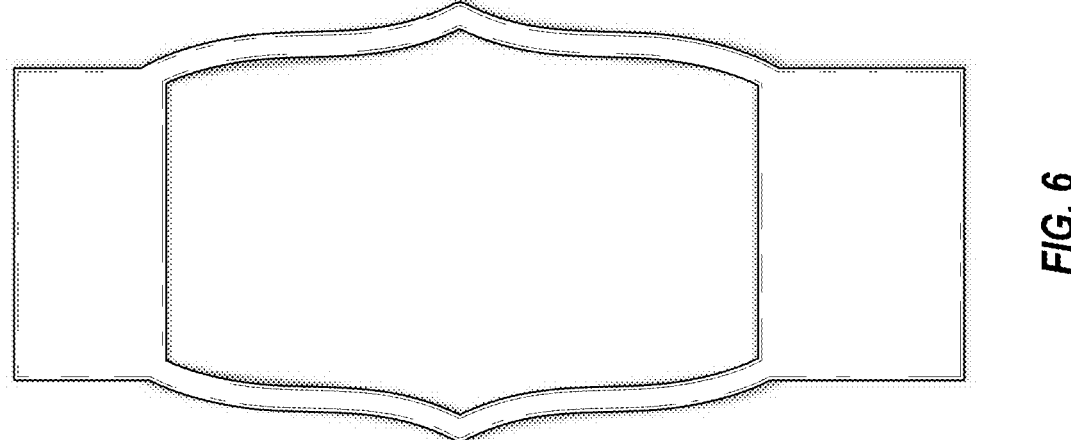
FIG. 6 depicts an example geometry after deformation which occurred during example experiments conducted in accordance with embodiments of the disclosed technology.

The linear fitting results of tensile stiffnesses of the rectangular geometry and the honeycomb geometries are presented by graph 500 FIG. 5. It should be mentioned that the stiffness of the honeycomb geometry may be derived from the linear least-squares fit of the stress-strain data after the geometry began to bear loads. In the example experiments, the stiffness of the honeycomb geometry was less than half of the stiffness of the rectangular geometry. This may be because the ring shape was not fully straightened after initial deformation, thereby causing the calculated stiffness result to be lower. The deformed configuration of geometry H captured by FE simulations is depicted in FIG. 6. The structure with longer r may exhibit lower stiffness because the angle between the adjacent ring elements is smaller. The results indicate that the honeycomb geometry with r=10.0 mm may be suited for ankle braces because in the example experiments it exhibited linear stiffness before being strained to 20%.

Geometrical Design and Stiffness

Although the honeycomb geometry can mimic the nonlinear behavior of an ankle ligament, its inherent stiffness may not be sufficient to fully protect large and/or fast ankle ROM. Therefore, stiffness and the mechanical response of each honeycomb geometry with different t's (see geometries $t_1$, H, $t_2$, and $t_3$ in table 200 of FIG. 2) and w's (see geometries H, $w_1$, and $w_2$ in table 200 of FIG. 2) were characterized in example experiments. The load-strain curves of thin geometries ($t_1$ and H) are shown in graph 700 of FIG. 7. The thicker geometries ($t_2$ and $t_3$) also exhibited nonlinear behavior during initial loading before transforming into approximate linear behaviors at ~10% strain. On the other hand, the mechanical behavior of the honeycomb geometry became linear by increasing w, as shown in graph 702 of FIG. 7.

Figure 7:
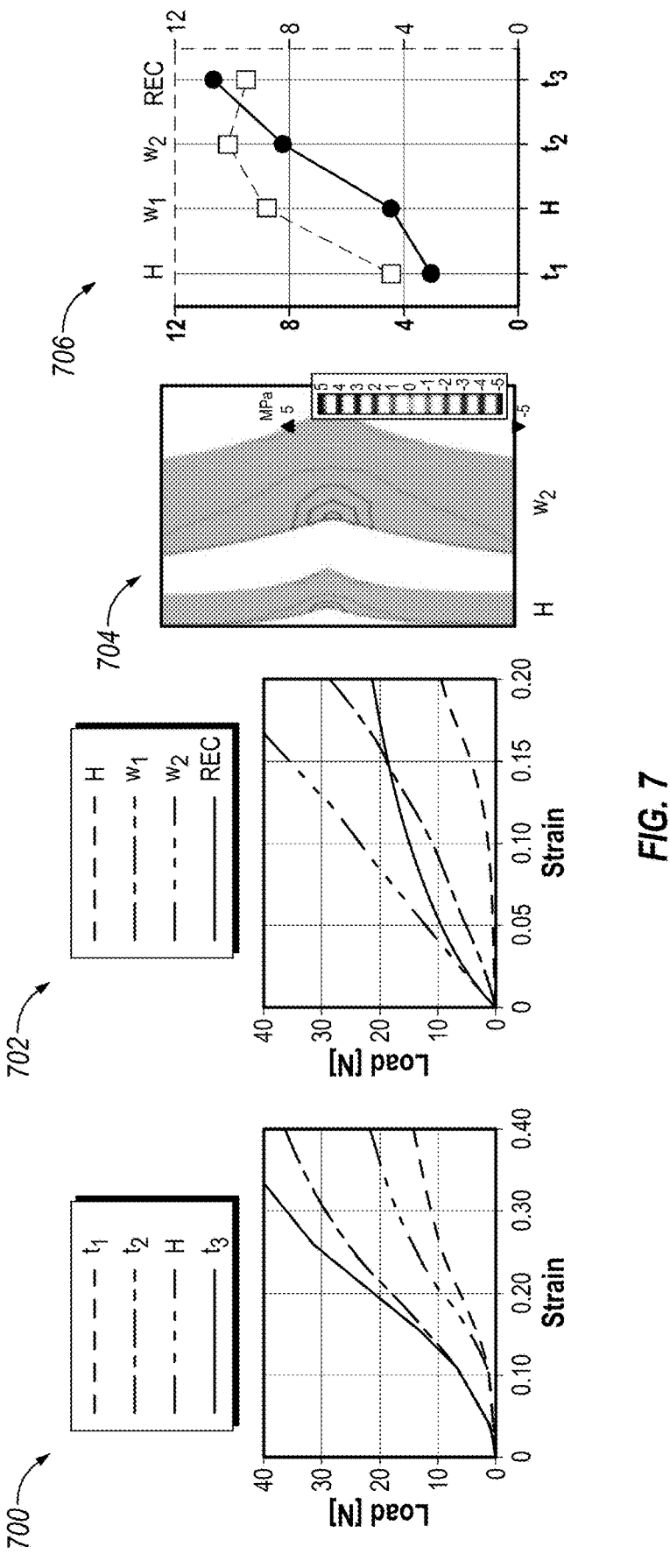
FIG. 7 depicts a series of graphs which illustrate data from example experiments conducted in accordance with embodiments of the disclosed technology.

The stress distribution along the ring elements of the honeycomb geometries was calculated using FE model simulation at 10% strain, and the result is shown in graph 704 of FIG. 7. The angled ring elements were bent to be straightened, and the stress intensity near the ring tip increased as w increased. This may be because the moment of inertia in x direction was linearly proportional to w cubed. Therefore, ring shapes with thicker walls required larger force to be straightened in the example experiments. Thus, geometries with thicker w's may need a larger force to be engaged compared with thinner geometries.

In the example experiments, the tensile stiffness of the geometry increased when t or w increased, as shown in graph 706 of FIG. 7. By increasing t or w, the cross-sectional area of the geometry increased, which resulted in higher stiffness. It should be noted that although the cross-sectional area of geometry $w_2$ was larger than $t_3$, $t_3$ exhibited a higher stiffness. This may be because it takes more strain to load a wider geometry before it becomes engaged to start bearing loads, which results in a decreased calculated stiffness. Therefore, increasing t of the geometry may enhance the tensile stiffness effectively, as opposed to increasing w. Together, these results may indicate that mechanical metamaterials may be designed with ligament-like behavior and strain-stiffening properties.

Example Experimental Conclusions

As described above, example experiments were conducted where honeycomb geometries with nonlinear strain-stiffening mechanical properties suitable for the design of next-generation adaptive stiffness ankle braces were fabricated and tested. For example, the physical properties of honeycomb mechanical materials were varied to identify optimal parameters that led to strain-stiffening behavior. Uniaxial tension was applied to each geometry profile to characterize its nonlinear behavior. In the example experiments, the length of r enabled the geometry to change its shape until 10% to 25% strains without bearing substantial loads. Thereafter, the stiffness may be adjusted by controlling t and w. In certain example experiments, the high bending stiffness of the wider wall thickness hindered the nonlinear behavior of the geometry. These results may imply that the honeycomb geometry designed with r=10.0 mm, w=1.0 mm, and t=2.0 to 3.0 mm exhibited ligament-like behavior. Accordingly, a honeycomb geometry having these dimensions may be suitable for the design of adaptive ankle braces. Future experiments may investigate the target stiffness needed to prevent lateral ankle sprains while enhancing stiffness using different geometries like circular, zigzag, and multi-layered patterns. Prototype braces integrated with new geometries may also be assessed under cyclic inversion-eversion loading to verify the effectiveness of the mechanical material-based ankle braces.

Additional Experiments and Figures

Figure 8:
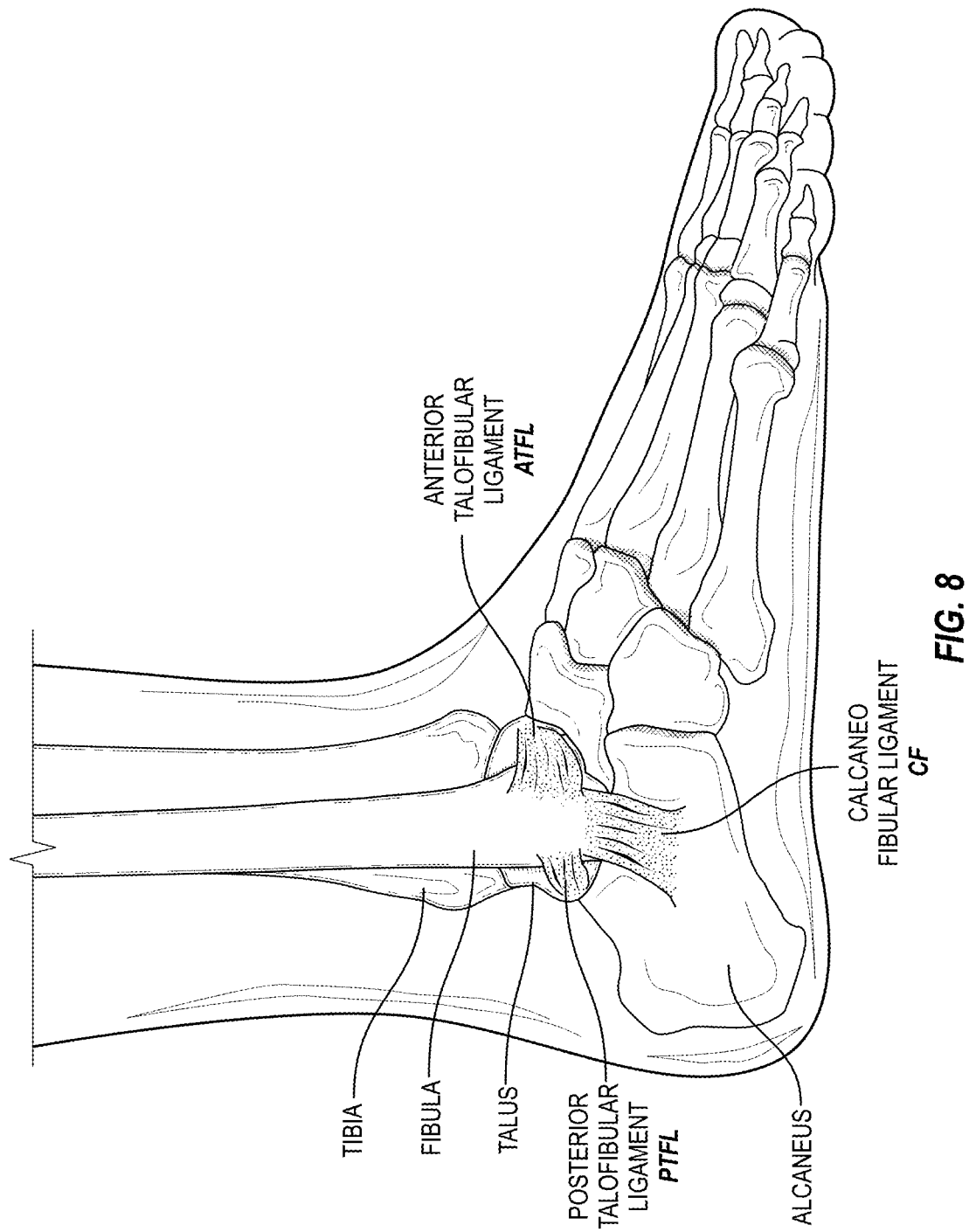
FIG. 8 depicts a diagram illustrating the lower leg and foot of an example patient, in accordance with embodiments of the disclosed technology.

FIG. 8 is a diagram illustrating the lower leg of an example patient, in accordance with various embodiments of the present disclosure. Among other items, the diagram illustrates the lateral ligaments of the example patient's ankle. These lateral ligaments include the posterior talofibular ligament (PTFL), the anterior talofibular ligament (ATFL), and the calcaneofibular ligament (CF).

Figure 9:
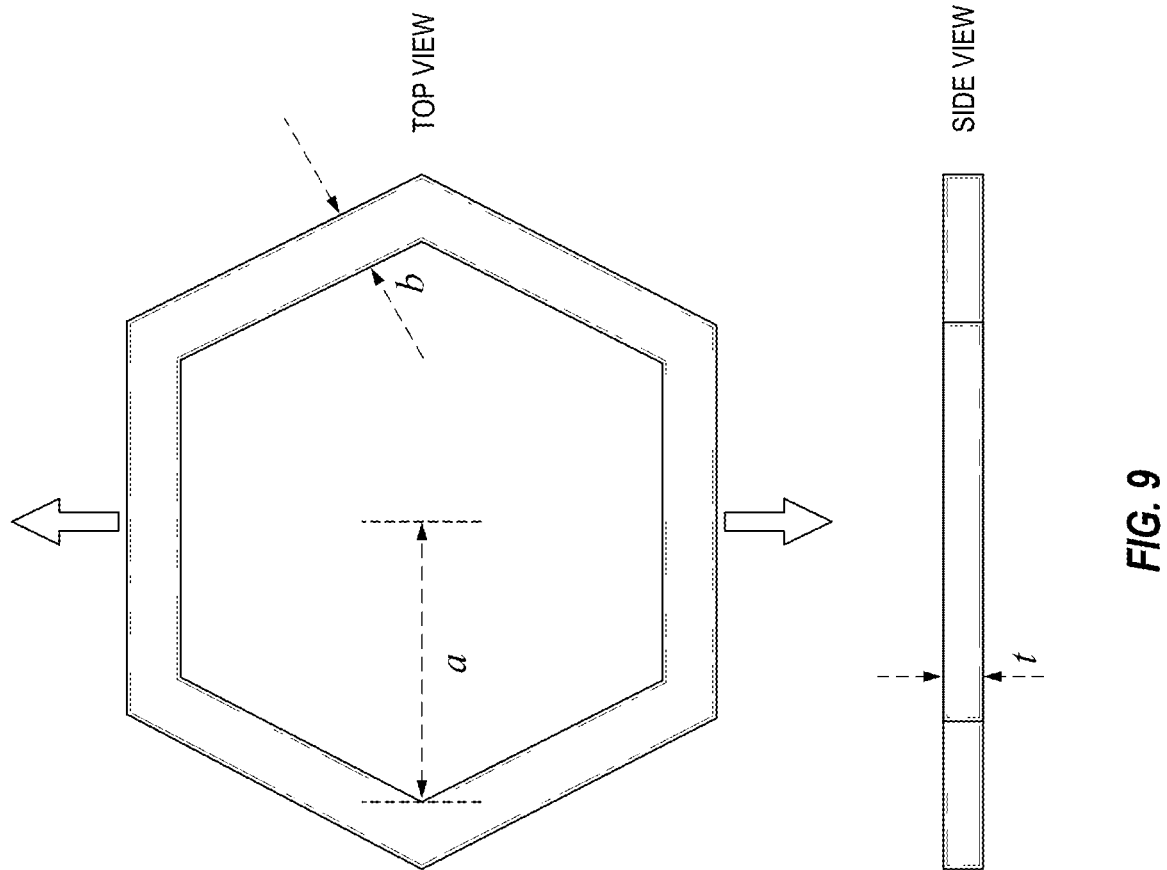
FIG. 9 depicts a diagram illustrating an example honeycomb metamaterial geometry for an ankle brace, in accordance with embodiments of the disclosed technology.

FIG. 9 is a diagram illustrating an example honeycomb metamaterial geometry for an ankle brace, in accordance with various embodiments of the present disclosure. As illustrated, the example honeycomb metamaterial geometry may have a ring size (a), a wall thickness (b), and a pattern thickness (t). In various embodiments, the pattern thickness can be varied to tune stiffness. As alluded to above, the honeycomb metamaterial may be comprised of TPU.

Figure 4:
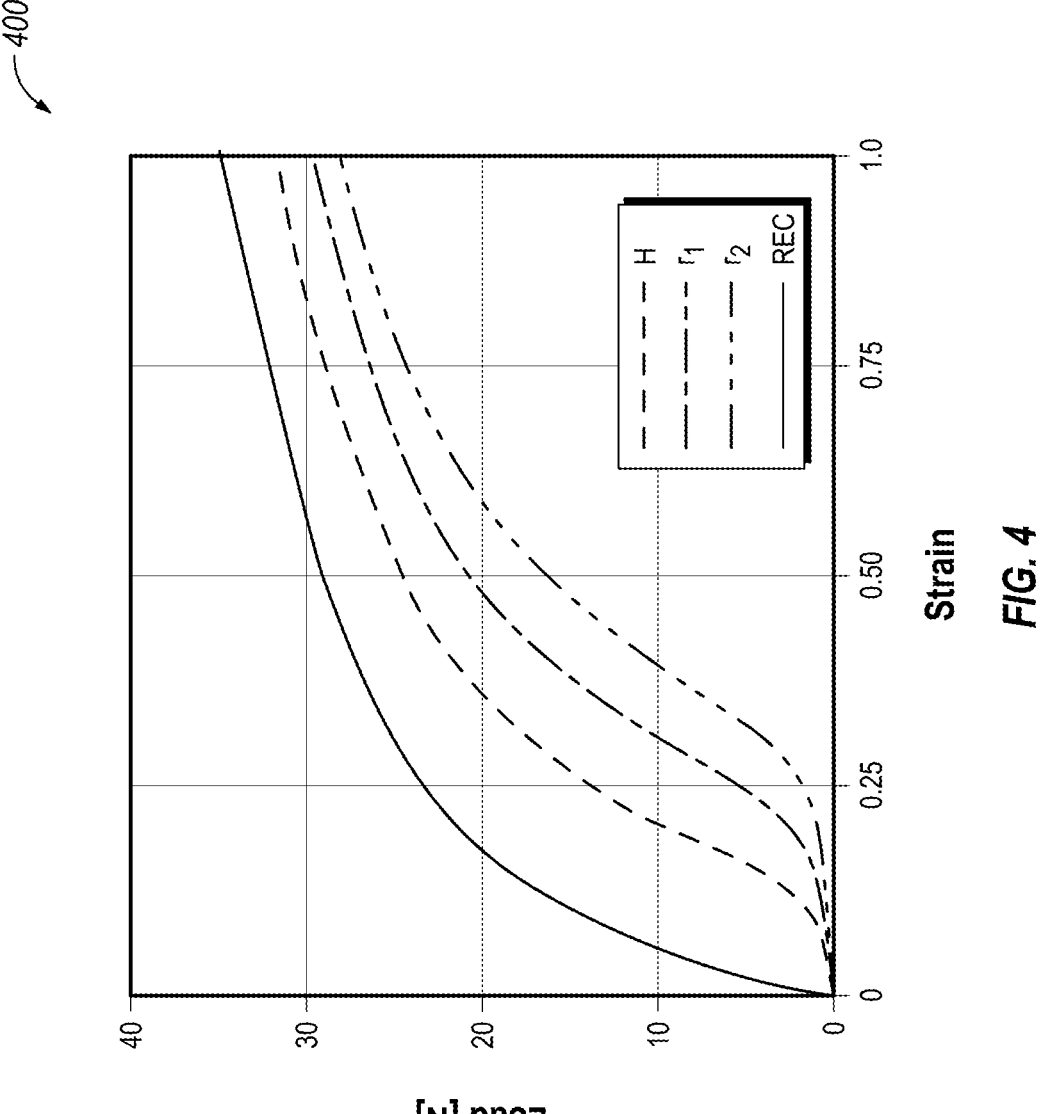
FIG. 4 depicts a graph which illustrates data from example experiments conducted in accordance with embodiments of the disclosed technology.
Figure 10:
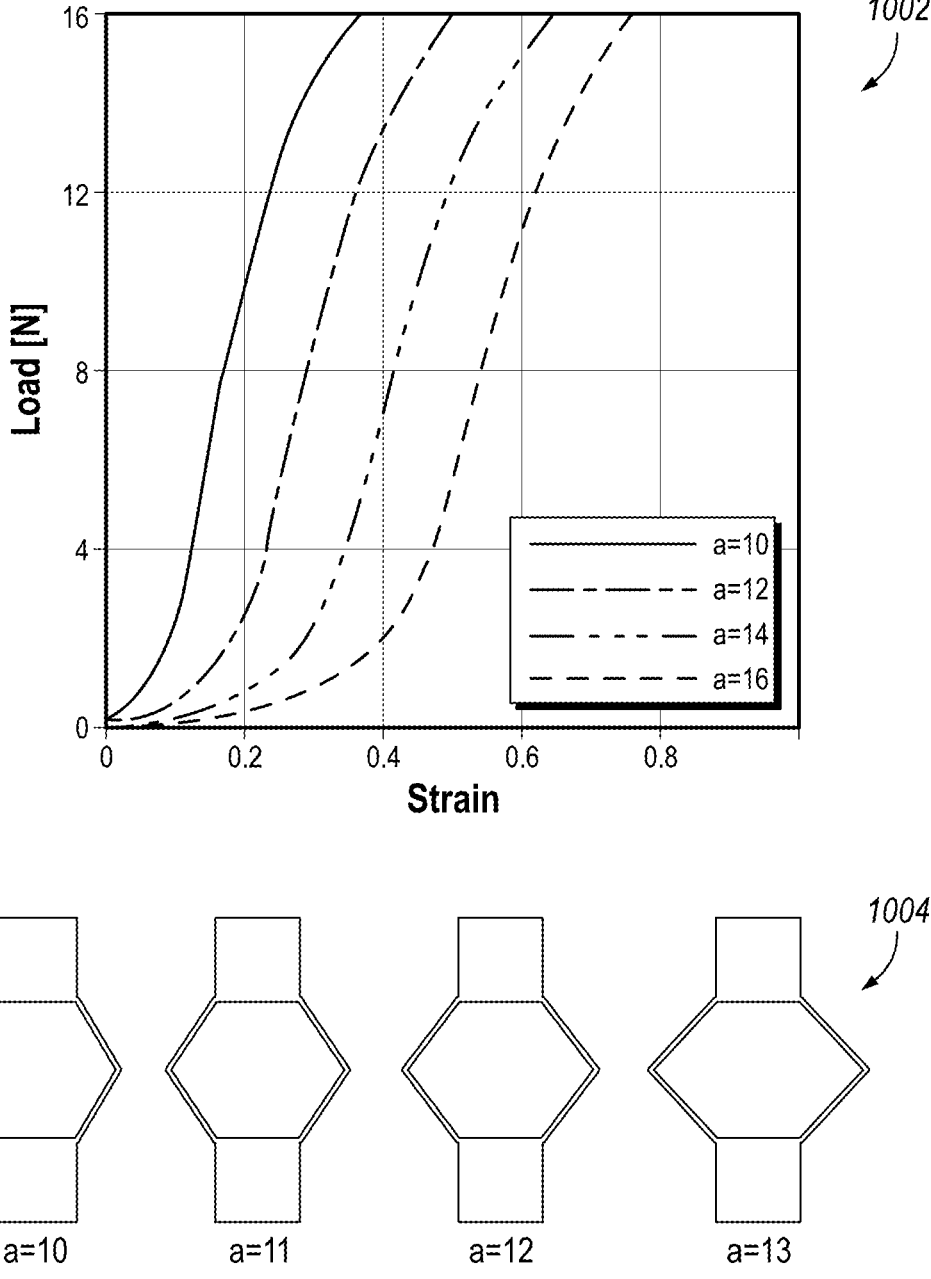
FIG. 10 depicts a graph and a diagram which illustrate example experiments conducted in accordance with embodiments of the disclosed technology.

FIG. 10 depicts a graph and a diagram which illustrate example experiments performed on example honeycomb metamaterial geometries for an ankle brace (such as the honeycomb metamaterial geometry for an ankle brace described in conjunction with FIG. 4), in accordance with various embodiments of the present disclosure. In these experiments, the wall thickness and the pattern thickness of the honeycomb metamaterial geometries were held constant, while ring size (a) was varied between 10.0 mm and 16.0 mm.

Graph 1002 illustrates the results from these example experiments.

Diagram 1004 illustrates the different ring sizes (a) for the example honeycomb metamaterial geometries which were tested.

Figure 11:
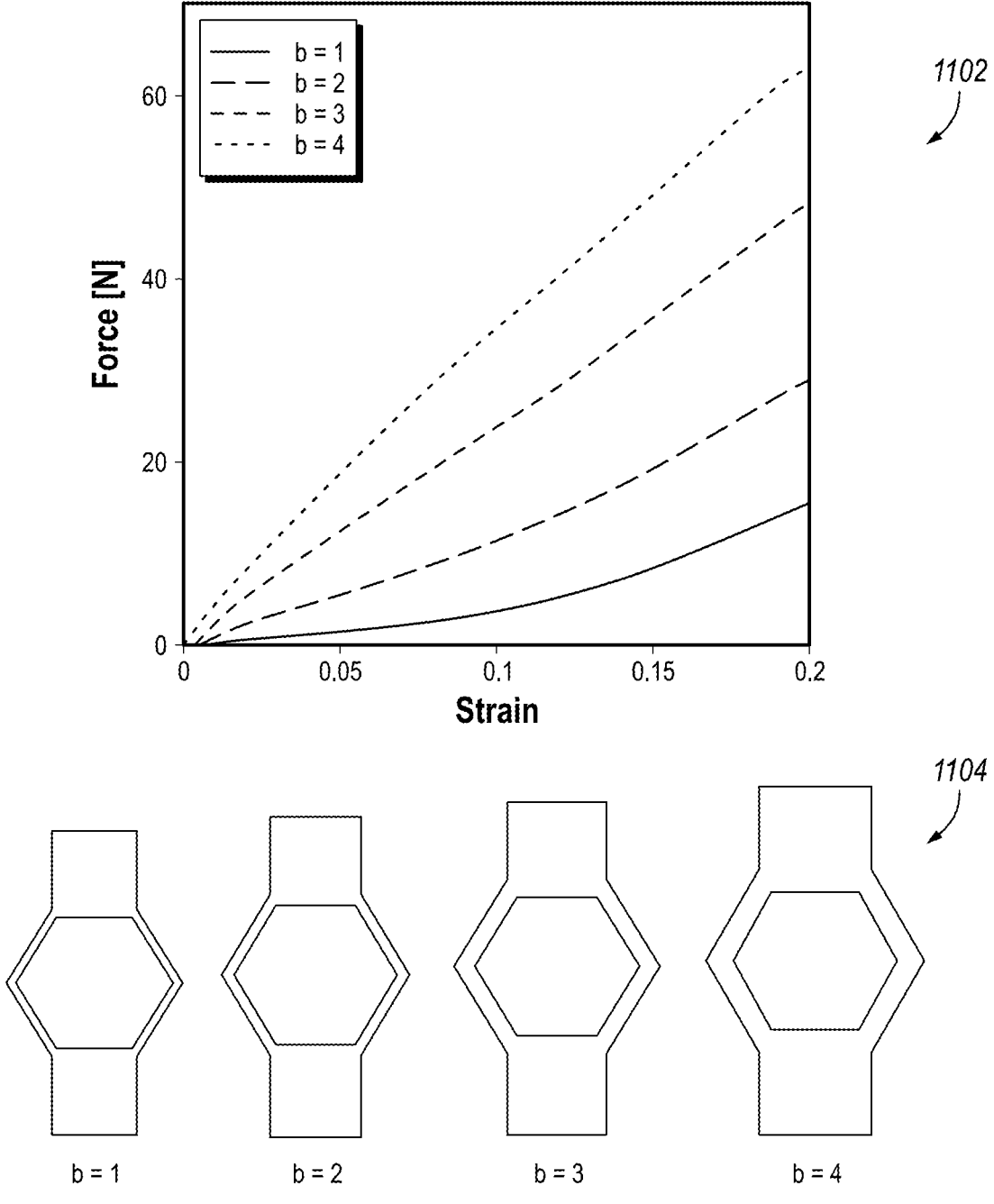
FIG. 11 depicts a graph and a diagram which illustrate example experiments conducted in accordance with embodiments of the disclosed technology.

FIG. 11 depicts a graph and a diagram which illustrate example experiments performed on example honeycomb metamaterial geometries for an ankle brace, in accordance with various embodiments of the present disclosure. In these experiments, the ring size and the pattern thickness of the honeycomb metamaterial geometries were held constant, while wall thickness (b) was varied between 1.0 mm and 4.0 mm.

Graph 1102 illustrates the results from these example experiments. As illustrated, in the example experiments stiffness increased as a function of wall thickness. In addition, the geometries with wide wall thickness were not able to sustain load-free shape change.

Diagram 1104 illustrates the different wall thicknesses (b) for the example honeycomb metamaterial geometries which were tested.

Figure 12:
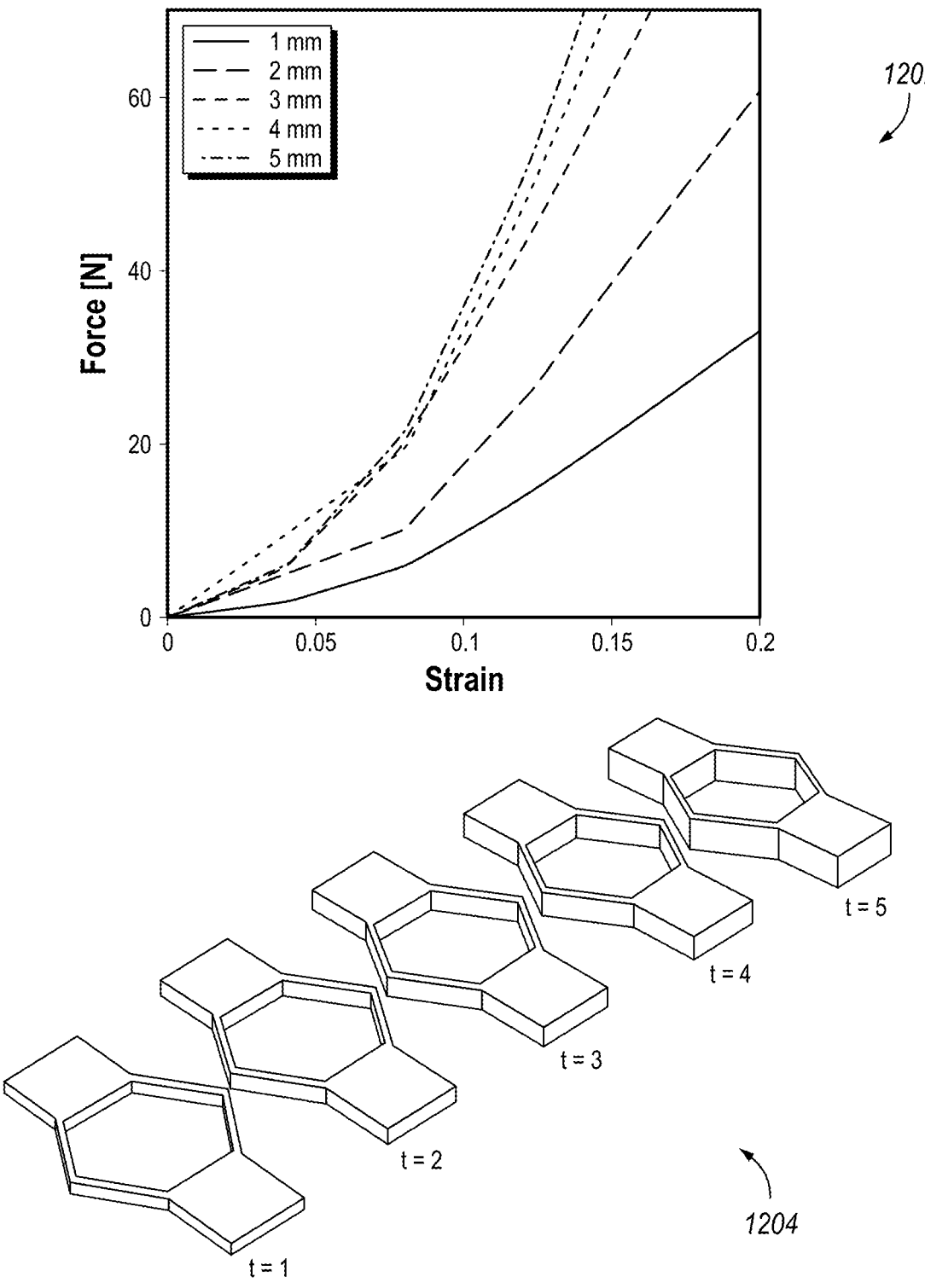
FIG. 12 depicts a graph and a diagram which illustrate example experiments conducted in accordance with embodiments of the disclosed technology.

FIG. 12 depicts a graph and a diagram which illustrate example experiments performed on example honeycomb metamaterial geometries for an ankle brace, in accordance with various embodiments of the present disclosure. In these experiments, the ring size and the wall thickness of the honeycomb metamaterial geometries were held constant, while pattern thickness (t) was varied between 1.0 mm and 5.0 mm.

Graph 1202 illustrates the results from these example experiments. As illustrated, in the example experiments stiffness increased as a function of pattern thickness.

Diagram 1204 illustrates the different pattern thicknesses (t) for the example honeycomb metamaterial geometries which were tested.

Figure 13:
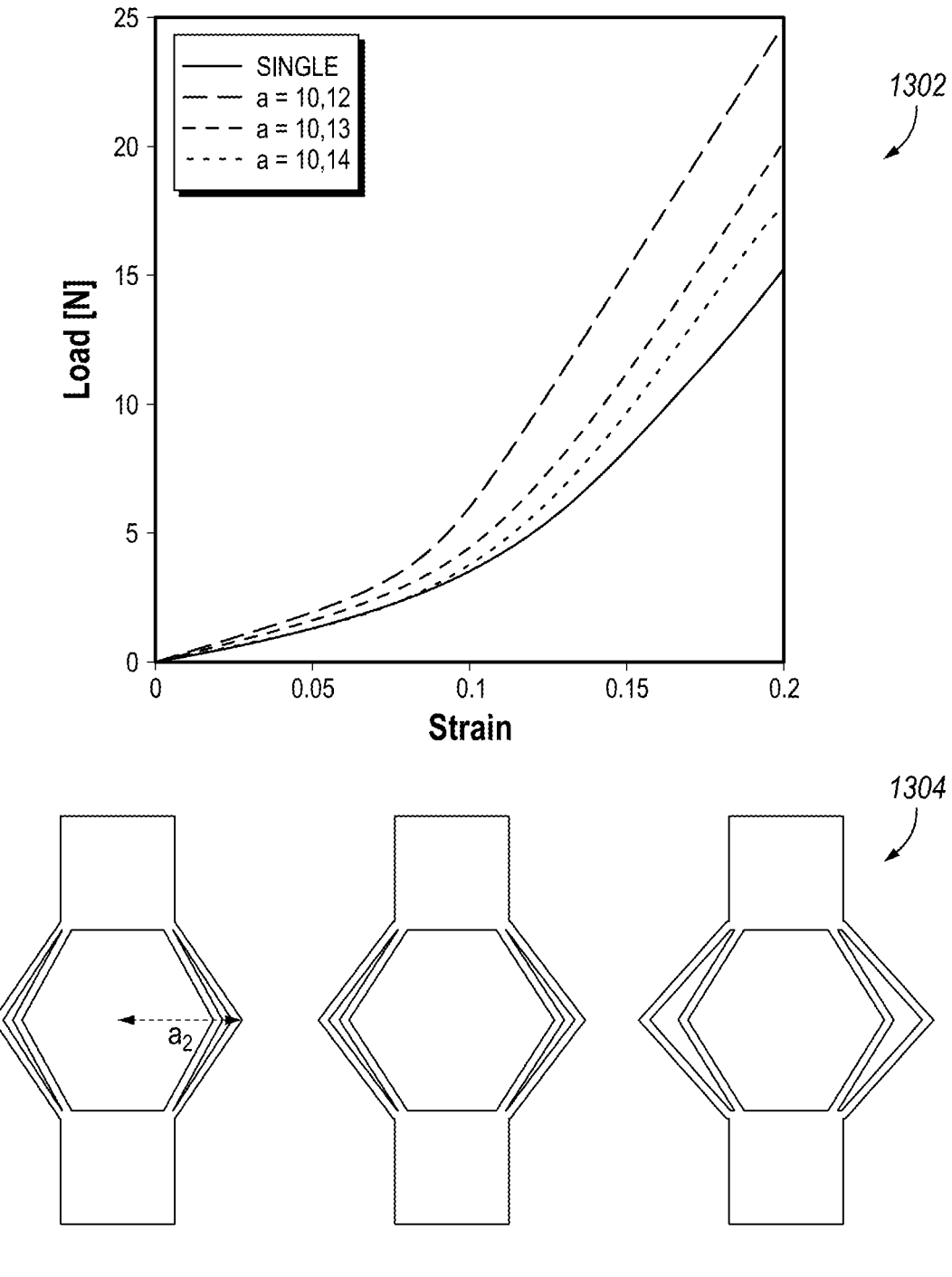
FIG. 13 depicts a graph and a diagram which illustrate example experiments conducted in accordance with embodiments of the disclosed technology.

FIG. 13 depicts a graph and a diagram which illustrate example experiments performed on example honeycomb metamaterial geometries for an ankle brace, in accordance with various embodiments of the present disclosure. In these experiments, double-walled ring geometries were tested. The inner ring size ($a_1$) was held constant at 10.0 mm, and the outer ring size ($a_2$) was varied between 12.0 mm and 14.0 mm.

Graph 1302 illustrates the results from these example experiments. In the example experiments stiffness increased when a second ring was added to the honeycomb structure.

Diagram 1304 illustrates the double-walled honeycomb metamaterial geometries of varying outer ring size which were tested.

Figure 14:
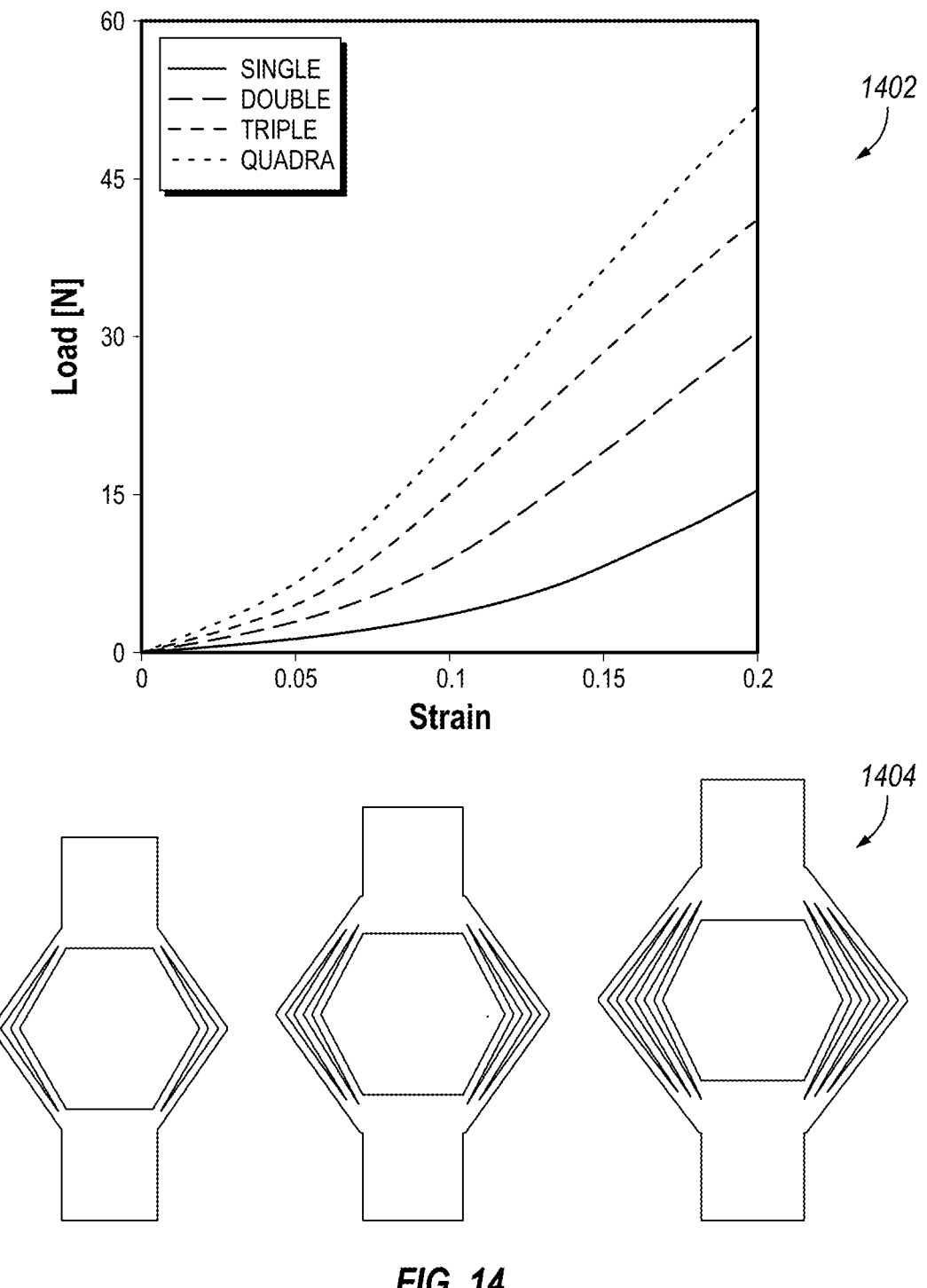
FIG. 14 depicts a graph and a diagram which illustrate example experiments conducted in accordance with embodiments of the disclosed technology.

FIG. 14 depicts a graph and a diagram which illustrate example experiments performed on example honeycomb metamaterial geometries for an ankle brace, in accordance with various embodiments of the present disclosure. In these experiments, multi-walled ring geometries were tested. In particular, double-wall, triple-wall, and quadra-wall geometries were tested.

Graph 1402 illustrates the results from these example experiments. In the example experiments stiffness increased as additional rings were added.

Diagram 1404 illustrates the multi-walled honeycomb metamaterial geometries which were tested.

Figure 15:
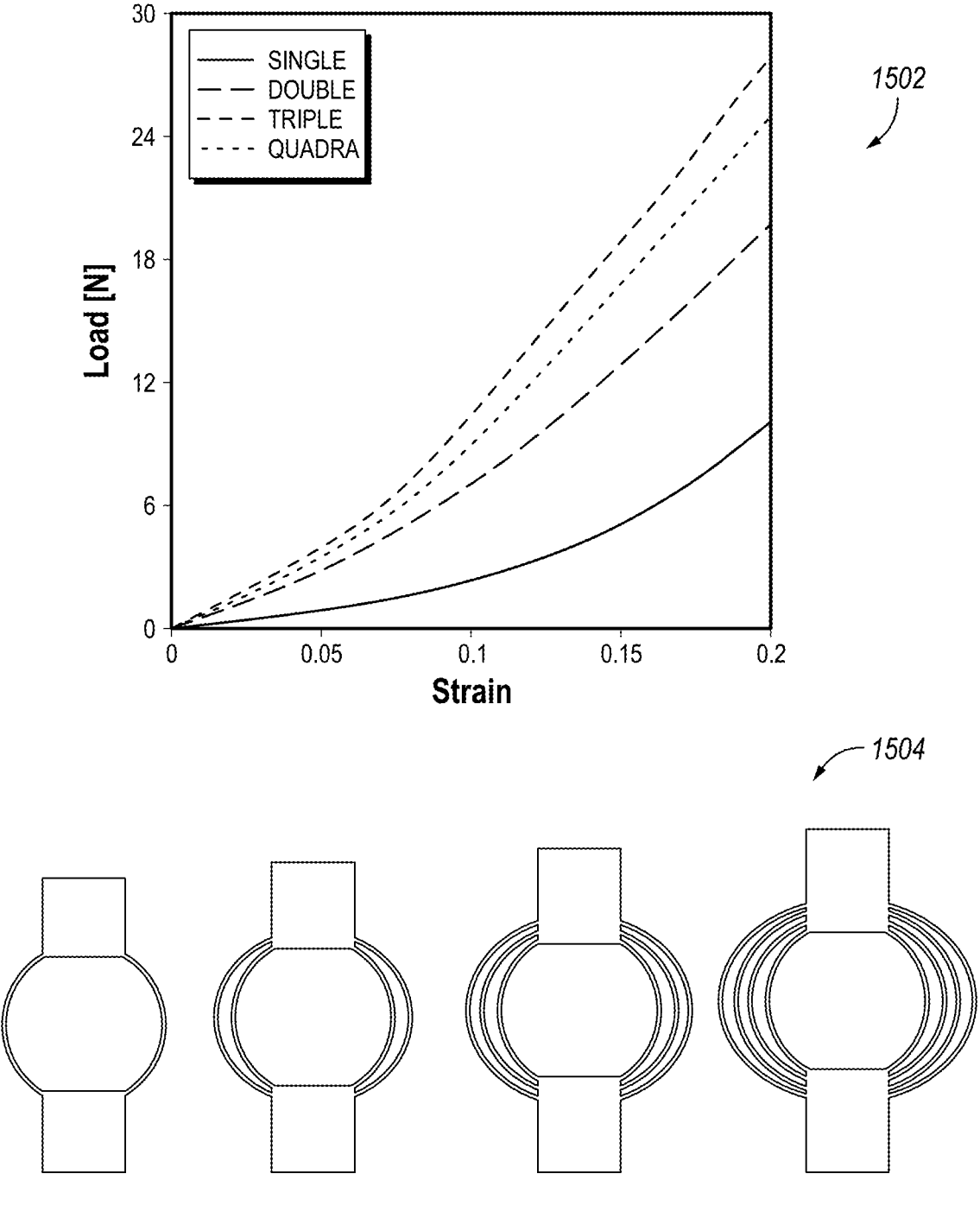
FIG. 15 depicts a graph and a diagram which illustrate example experiments conducted in accordance with embodiments of the disclosed technology.

FIG. 15 depicts a graph and a diagram which illustrate example experiments performed on example metamaterial geometries for an ankle brace, in accordance with various embodiments of the present disclosure. In these experiments, circular multi-walled structure were tested.

Graph 1502 illustrates the results from these example experiments.

Diagram 1504 illustrates the circular multi-walled metamaterial geometries which were tested.

Figure 16:
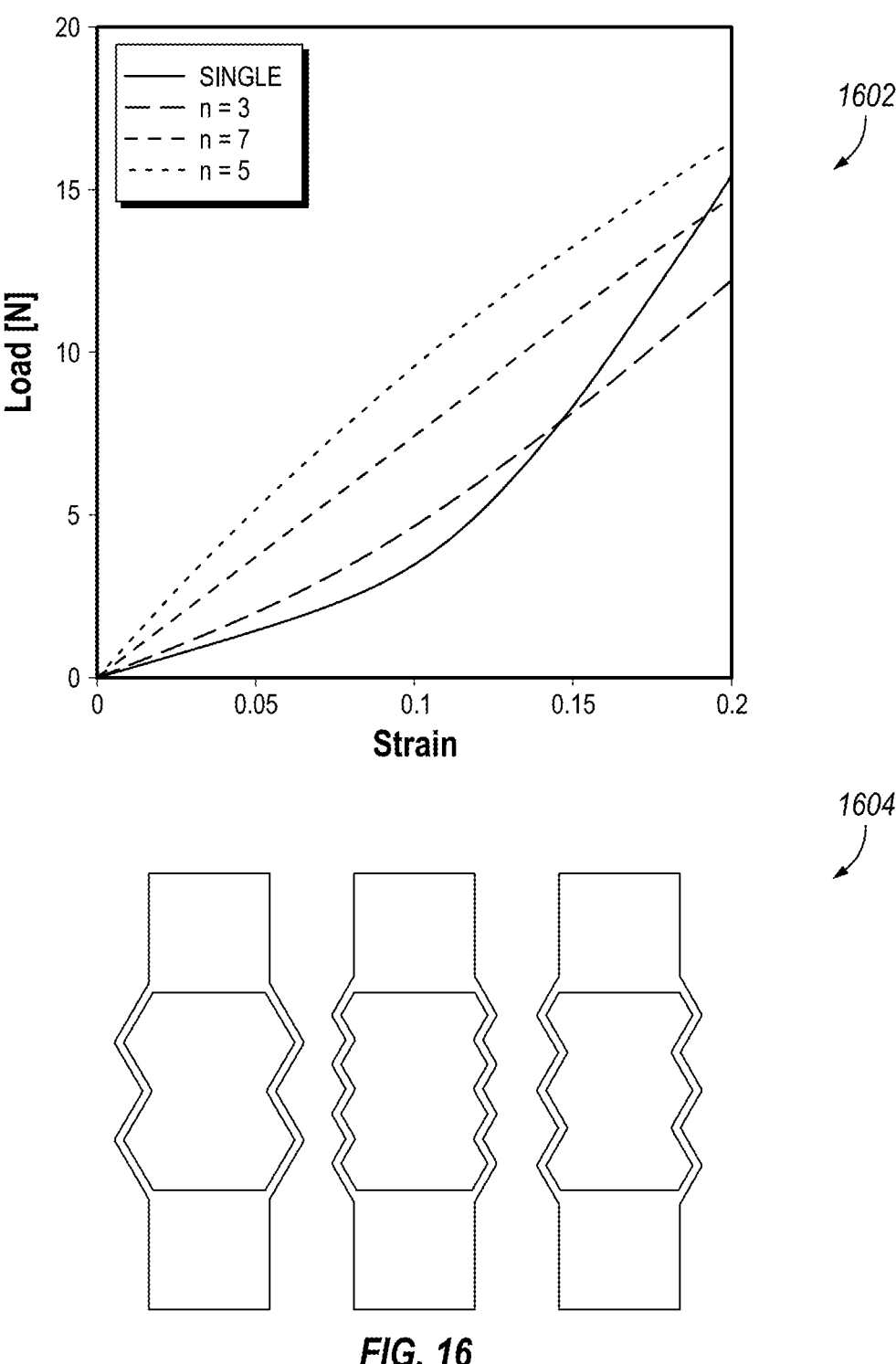
FIG. 16 depicts a graph and a diagram which illustrate example experiments conducted in accordance with embodiments of the disclosed technology.

FIG. 16 depicts a graph and a diagram which illustrate example experiments performed on example metamaterial geometries for an ankle brace, in accordance with various embodiments of the present disclosure. In these experiments, structures with turning points were tested.

Graph 1602 illustrates the results from these example experiments.

Diagram 1604 illustrates the metamaterial geometries with turning points, which were tested.

FIG. 17 illustrates an example adaptive-stiffness ankle brace 1700 and an example diagram 1750 of an ankle ligament region, in accordance with embodiments of the disclosed technology. As depicted in FIG. 17, adaptive-stiffness ankle brace 1700 includes an adaptive-stiffness metamaterial 1710 coupled to a flexible sleeve 1720. Adaptive-stiffness metamaterial 1710 may comprise a plurality of adjacent unit cells arranged in a manner that emulates the location and orientation of ankle ligaments. In particular: the arrangement of adjacent unit cells 1712(*a*)-(*c*) emulates the location/orientation of the posterior talofibular ligament (PTFL); the arrangement of adjacent unit cells 1714(*a*)-(*d*) and 1716(*a*)-(*e*) emulate the location/orientation of the larger calcaneofibular ligament (CF); and the arrangement of adjacent unit cells 1718(*a*)-(*e*) emulate the location/orientation of the anterior talofibular ligament (ATFL). As alluded to above, by emulating the location and orientation of ligaments in a ligament region, embodiments may more closely emulate the strain-stiffening behavior of ligaments in the ligament region. By emulating the strain-stiffening behavior of ligaments, embodiments can provide a more comfortable/natural fit than existing orthopedic braces.

As depicted, the plurality of adjacent unit cells comprising adaptive-stiffness metamaterial 1710 comprise hexagonal ring-shaped unit cells (sometimes referred to herein as a honeycomb design). Some or all of these hexagonal ring-shaped unit cells may be multi-walled (as described in conjunction with FIG. 13). In other words, a given hexagonal ring-shaped unit cell may comprise a first hexagonal ring concentrically-located within a second hexagonal ring, where the first hexagonal ring has a slightly smaller ring diameter than the second hexagonal ring.

While not depicted, adaptive-stiffness metamaterial 1710 may be coupled to flexible sleeve 1720 at junctions between adjacent unit cells of adaptive-stiffness metamaterial 1710.

Figure 18:
FIG. 18 illustrates an adaptive-stiffness brace, in accordance with embodiments of the disclosed technology.

FIG. 18 illustrates an adaptive-stiffness brace 1800, in accordance with embodiments of the disclosed technology. Similar to adaptive-stiffness ankle brace 1700, adaptive-stiffness brace 1800 includes an adaptive-stiffness metamaterial 1810 coupled to a flexible sleeve 1820. Adaptive-stiffness metamaterial 1810 comprises plurality of adjacent unit cells arranged on flexible sleeve 1820. Like the unit cells of adaptive-stiffness metamaterial 1710, the unit cells of adaptive-stiffness metamaterial 1810 comprise hexagonal ring-shaped unit cells.

Figure 19:
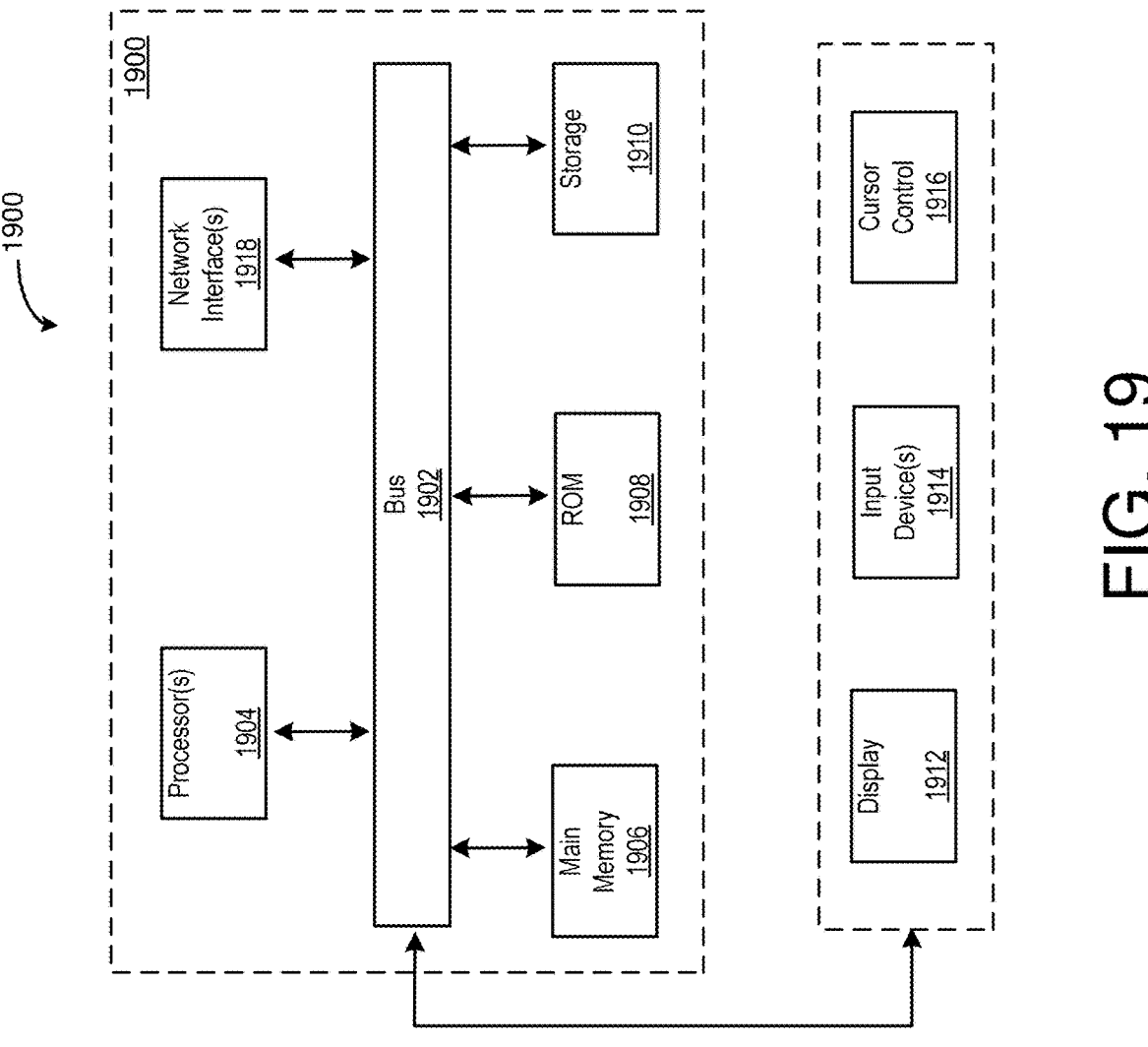
FIG. 19 depicts a block diagram of an example computer system in which various of the embodiments described herein may be implemented.

FIG. 19 depicts a block diagram of an example computer system 1900 in which various of the embodiments described herein may be implemented. The computer system 1900 includes a bus 1902 or other communication mechanism for communicating information, one or more hardware processors 1904 coupled with bus 1902 for processing information. Hardware processor(s) 1904 may be, for example, one or more general purpose microprocessors.

The computer system 1900 also includes a main memory 1906, such as a random access memory (RAM), cache and/or other dynamic storage devices, coupled to bus 1902 for storing information and instructions to be executed by processor 1904. Main memory 1906 also may be used for storing temporary variables or other intermediate information during execution of instructions to be executed by processor 1904. Such instructions, when stored in storage media accessible to processor 1904, render computer system 1900 into a special-purpose machine that is customized to perform the operations specified in the instructions.

The computer system 1900 further includes a read only memory (ROM) 1908 or other static storage device coupled to bus 1902 for storing static information and instructions for processor 1904. A storage device 1910, such as a magnetic disk, optical disk, or USB thumb drive (Flash drive), etc., is provided and coupled to bus 1902 for storing information and instructions.

The computer system 1900 may be coupled via bus 1902 to a display 1912, such as a liquid crystal display (LCD) (or touch screen), for displaying information to a computer user. An input device 1914, including alphanumeric and other keys, is coupled to bus 1902 for communicating information and command selections to processor 1904. Another type of user input device is cursor control 1916, such as a mouse, a trackball, or cursor direction keys for communicating direction information and command selections to processor 1904 and for controlling cursor movement on display 1912. In some embodiments, the same direction information and command selections as cursor control may be implemented via receiving touches on a touch screen without a cursor.

The computing system 1900 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "engine," "system," "database," data store," and the like, as used herein, can refer to logic embodied in hardware or firmware, or to a collection of software instructions, possibly having entry and exit points, written in a programming language, such as, for example, Java, C or C++. A software component may be compiled and linked into an executable program, installed in a dynamic link library, or may be written in an interpreted programming language such as, for example, BASIC, Perl, or Python. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computer system 1800 may implement the techniques described herein using customized hard-wired logic, one or more ASICs or FPGAs, firmware and/or program logic which in combination with the computer system causes or programs computer system 1800 to be a special-purpose machine. According to one embodiment, the techniques herein are performed by computer system 1800 in response to processor(s) 1804 executing one or more sequences of one or more instructions contained in main memory 1806. Such instructions may be read into main memory 1806 from another storage medium, such as storage device 1810. Execution of the sequences of instructions contained in main memory 1806 causes processor(s) 1804 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 1810. Volatile media includes dynamic memory, such as main memory 1806. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 1802. Transmission media can also take the form of acoustic or light waves, such as those generated during radio-wave and infra-red data communications.

The computer system 1800 also includes a communication interface 1818 coupled to bus 1802. Network interface 1818 provides a two-way data communication coupling to one or more network links that are connected to one or more local networks. For example, communication interface 1818 may be an integrated services digital network (ISDN) card, cable modem, satellite modem, or a modem to provide a data communication connection to a corresponding type of telephone line. As another example, network interface 1818 may be a local area network (LAN) card to provide a data communication connection to a compatible LAN (or WAN component to communicated with a WAN). Wireless links may also be implemented. In any such implementation, network interface 1818 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet." Local network and Internet both use electrical, electromagnetic or optical signals that carry digital data streams. The signals through the various networks and the signals on network link and through communication interface 1818, which carry the digital data to and from computer system 1800, are example forms of transmission media.

The computer system 1800 can send messages and receive data, including program code, through the network (s), network link and communication interface 1818. In the Internet example, a server might transmit a requested code for an application program through the Internet, the ISP, the local network and the communication interface 1818.

The received code may be executed by processor 1804 as it is received, and/or stored in storage device 1810, or other non-volatile storage for later execution.

Each of the processes, methods, and algorithms described in the preceding sections may be embodied in, and fully or partially automated by, code components executed by one or more computer systems or computer processors comprising computer hardware. The one or more computer systems or computer processors may also operate to support performance of the relevant operations in a "cloud computing" environment or as a "software as a service" (Saas). The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. The methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, a circuit might be implemented utilizing any form of hardware, software, or a combination thereof. For example, one or more processors, controllers, ASICs, PLAS, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto, such as computer system 1800.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent component names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the components or functionality described or claimed as part of the component are all configured in a common package. Indeed, any or all of the various components of a component, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. An adaptive-stiffness brace comprising:
 a flexible sleeve to be worn over a ligament region; and
 an adaptive-stiffness metamaterial coupled to the flexible sleeve, the adaptive-stiffness metamaterial comprising adjacent unit cells arranged on the flexible sleeve to emulate strain-stiffening behavior of ligaments in the ligament region;
 wherein the adjacent unit cells are geometrically arranged on the flexible sleeve to emulate location and orientation of the ligaments in the ligament region.

2. The adaptive-stiffness brace of claim 1, wherein the adaptive-stiffness metamaterial exhibits increased stiffness under increased strain.

3. The adaptive-stiffness brace of claim 2, wherein the adaptive-stiffness metamaterial exhibits non-linear strain-stiffening behavior.

4. The adaptive-stiffness brace of claim 1, wherein the adjacent unit cells comprise of adjacent hexagonal ring-shaped unit cells.

5. The adaptive-stiffness brace of claim 4, wherein a hexagonal ring-shaped unit cell comprises a first hexagonal ring concentrically located within a second hexagonal ring.

6. The adaptive-stiffness brace of claim 1, wherein the adaptive-stiffness metamaterial is coupled to the flexible sleeve at junctions of the adjacent unit cells.

7. The adaptive-stiffness brace of claim 1, wherein the adaptive-stiffness metamaterial comprises a flexible polymer material.

8. The adaptive-stiffness brace of claim 7, wherein the flexible polymer material comprises thermoplastic polyurethane.

9. The adaptive-stiffness brace of claim 1, wherein:
 the ligament region is an ankle; and the adjacent unit cells are geometrically arranged on the flexible sleeve to emulate location and orientation of ankle ligaments.

10. The adaptive-stiffness brace of claim 1, wherein the adjacent unit cells are geometrically arranged on the flexible sleeve to emulate location and orientation of ankle ligaments such that:

a first subset of the adjacent unit cells are geometrically arranged to emulate the location and orientation of a posterior talofibular ligament (PTFL) of an ankle;

a second subset of the adjacent unit cells are geometrically arranged to emulate the location and orientation of a calcaneofibular ligament (CFL) of the ankle; and a third subset of the adjacent unit cells are geometrically arranged to emulate the location and orientation of an anterior talofibular ligament (ATFL) of the ankle.

11. An adaptive-stiffness metamaterial configured to be assembled onto an orthopedic brace, the adaptive-stiffness metamaterial comprising:

adjacent ring-shaped unit cells arranged to emulate strain-stiffening behavior of ligaments of a ligament region;

wherein the adaptive-stiffness metamaterial exhibits increased stiffness under increased strains;

wherein a respective ring-shaped unit cell comprises a first ring concentrically located within a second ring; and wherein the first ring and the second ring of the respective ring-shaped unit cell are disposed across a common layer of the adjacent ring-shaped unit cells.

12. The adaptive-stiffness metamaterial of claim 11, wherein the adjacent ring-shaped unit cells comprise adjacent hexagonal ring-shaped unit cells.

13. The adaptive-stiffness metamaterial of claim 12, wherein the first ring of the respective ring-shaped unit cell comprises a first hexagonal ring and the second ring of the respective ring-shaped unit cell comprises a second hexagonal ring.

14. The adaptive-stiffness metamaterial of claim 11, wherein the adaptive-stiffness metamaterial comprises a flexible polymer material.

15. The adaptive-stiffness metamaterial of claim 14, wherein the flexible polymer material comprises thermoplastic polyurethane.

16. The adaptive-stiffness metamaterial of claim 11, wherein:

the adjacent ring-shaped unit cells are arranged to emulate strain-stiffening behavior of ankle ligaments.

17. An adaptive-stiffness brace comprising:

a flexible sleeve to be worn over a ligament region; and an adaptive-stiffness metamaterial coupled to the flexible sleeve, wherein:

the adaptive-stiffness metamaterial comprises adjacent ring-shaped unit cells, a respective ring-shaped unit cell comprises a first ring concentrically located within a second ring, the first ring and the second ring of the respective ring-shaped unit cell are disposed across a common layer of the adjacent ring-shaped unit cells, and the adaptive-stiffness metamaterial exhibits increased stiffness under increased strains.

18. The adaptive-stiffness brace of claim 17, wherein the adjacent ring-shaped unit cells comprise adjacent hexagonal ring-shaped unit cells.

19. The adaptive-stiffness brace of claim 17, wherein the adjacent ring-shaped unit cells are arranged on the flexible sleeve to emulate strain-stiffening behavior of ligaments of the ligament region.

20. The adaptive-stiffness brace of claim 19, wherein:

the ligament region is an ankle; and the adjacent ring-shaped unit cells are arranged on the flexible sleeve to emulate strain-stiffening behavior of ankle ligaments.

* * * * *